United States Patent
Nolt et al.

(10) Patent No.: US 10,327,942 B2
(45) Date of Patent: Jun. 25, 2019

(54) SHOULDER BRACES AND METHODS OF USE

(71) Applicant: Derek Nolt, Edmonton (CA)

(72) Inventors: Derek Nolt, Edmonton (CA); Bryce Borgel, Edmonton (CA)

(73) Assignee: Derek Nolt, Edmonton (CA)

( * ) Notice: Subject to any disclaimer, the term of this patent is extended or adjusted under 35 U.S.C. 154(b) by 464 days.

(21) Appl. No.: 15/166,107

(22) Filed: May 26, 2016

(65) Prior Publication Data

US 2017/0231799 A1    Aug. 17, 2017

(30) Foreign Application Priority Data

Feb. 12, 2016    (CA) .................................. 2920670

(51) Int. Cl.
*A61F 5/058*    (2006.01)
*A61F 5/01*     (2006.01)

(52) U.S. Cl.
CPC ........ *A61F 5/05808* (2013.01); *A61F 5/0102* (2013.01)

(58) Field of Classification Search
CPC .............. A61F 5/05841; A61F 5/05858; A61F 5/3715; A61F 5/37; A61F 5/01; A61F 5/05808; A61F 5/0102
See application file for complete search history.

(56) References Cited

U.S. PATENT DOCUMENTS

| | | | |
|---|---|---|---|
| 139,366 A | 5/1873 | Burnap | |
| 198,503 A | 12/1877 | Altmann | |
| 531,372 A | 12/1894 | Gamble | |
| 665,688 A | 1/1901 | Hollem | |
| 877,560 A | 1/1908 | Foltz | |
| 903,403 A * | 11/1908 | Quick | ..................... A61F 5/028 2/44 |

(Continued)

FOREIGN PATENT DOCUMENTS

| | | |
|---|---|---|
| CN | 202020087 | 11/2011 |
| CN | 203055108 | 7/2013 |

(Continued)

OTHER PUBLICATIONS

International Search Report dated May 30, 2017 on the corresponding P.C.T. patent application No. PCT/CA2017/050159 filed Feb. 10, 2017, 4 pages.

(Continued)

*Primary Examiner* — Ophelia A Hawthorne
(74) *Attorney, Agent, or Firm* — Robert A. Nissen

(57) ABSTRACT

A shoulder brace has: a support structure; strap retractors such as flat spiral torsion springs mounted to the support structure; and left and right shoulder straps each having a first strap part connected to the support structure and a second strap part connected to a free end of a respective spiral torsion spring. A method has the following stages: positioning a support structure against a user's upper back; looping left and right shoulder straps around a user's left and right shoulders, respectively; and in which each of the left and right shoulder straps connects to the support structure via a strap retractor, such as a spiral torsion spring for applying tension through the respective left or right shoulder strap to pull the user's shoulders back.

20 Claims, 11 Drawing Sheets

(56) References Cited

U.S. PATENT DOCUMENTS

| | | | |
|---|---|---|---|
| 1,544,162 | A | 6/1925 | La Vigne |
| 1,678,584 | A | 7/1928 | Branson |
| 1,722,205 | A | 7/1929 | Freund |
| 2,450,298 | A | 9/1948 | Peterson et al. |
| 2,906,260 | A | 9/1959 | Myers |
| 3,277,889 | A | 10/1966 | Palmer |
| 3,499,441 | A | 3/1970 | Hall |
| 3,548,818 | A | 12/1970 | Kaplan |
| 3,718,137 | A | 2/1973 | Gaylord |
| 3,856,004 | A | 12/1974 | Cox |
| 3,857,388 | A | 12/1974 | Frankel |
| 4,018,189 | A | 4/1977 | Umphries et al. |
| 4,527,289 | A | 7/1985 | Shea |
| 4,570,619 | A | 2/1986 | Gamm |
| 4,589,406 | A | 5/1986 | Florek |
| 5,067,484 | A | 11/1991 | Hiemstra-Paez |
| 5,133,340 | A | 7/1992 | Koopmann |
| 5,816,251 | A | 10/1998 | Glisan |
| 5,860,944 | A | 1/1999 | Hoffman, Jr. |
| 6,315,747 | B1 | 11/2001 | Toole |
| 6,840,916 | B2 | 1/2005 | Kozersky |
| 6,991,611 | B2 | 1/2006 | Rhee |
| 7,901,371 | B1 | 3/2011 | Vayntraub |
| 7,954,204 | B2 | 6/2011 | Hammerslag et al. |
| 8,328,742 | B2 | 12/2012 | Bledsoe |
| 8,556,840 | B2 | 10/2013 | Burke et al. |
| D748,277 | S | 1/2016 | Chen |
| 2006/0129076 | A1 | 6/2006 | Haneda |
| 2011/0152737 | A1 | 6/2011 | Burke et al. |
| 2012/0078149 | A1 | 3/2012 | Azimzadeh |
| 2013/0110021 | A1 | 5/2013 | Liu et al. |
| 2013/0317400 | A1 | 11/2013 | Ferezy |
| 2014/0039370 | A1 | 2/2014 | Sears |
| 2014/0074003 | A1 | 3/2014 | Monden |
| 2014/0100501 | A1 | 4/2014 | Burke et al. |
| 2014/0135674 | A1 | 5/2014 | Kirk |
| 2014/0221893 | A1 | 8/2014 | Modglin |
| 2015/0282974 | A1 | 10/2015 | Kamenaga et al. |

FOREIGN PATENT DOCUMENTS

| | | |
|---|---|---|
| CN | 205459292 | 8/2016 |
| EP | 2070495 | 6/2009 |
| FR | 2880797 | 7/2006 |
| GB | 190228447 | 10/1903 |
| GB | 379185 | 8/1932 |
| KR | 20110124846 | 11/2011 |
| NL | 1039802 | 3/2014 |
| TW | I384972 | 2/2013 |

OTHER PUBLICATIONS

Landmark Medical Systems, Clavicle Brace, URL =http://landmark-medical-systems.myshopify.com/collections/arm-shoulder/products/clavicle-brace, accessed on Feb. 1, 2016, 2 pages.

Landmark Medical Systems, MKO Pulley Back Brace, URL =http://landmark-medical-systems.myshopify.com/products/mko-pulley-back-brace, accessed on Dec. 21, 2015, 1 page.

Medicalbroker, Thuasne Ligaflex clavicular support brace, URL =http://e-medicalbroker.com/product-eng-3855-Thuasne-Ligaflex-clavicular-support-brace.html, accessed on Feb. 1, 2016, 7 pages.

Screenshots taken from the WayBack Machine of the Ergo BackSupport website as of Jan. 13, 2016, URL=http://web.archive.org/web/20160113193915/http://ergobacksupport.com/, information accessed on Aug. 29, 2016, 7 pages.

\* cited by examiner

SHOULDER BRACES AND METHODS OF USE

CROSS-REFERENCE TO RELATED APPLICATIONS

This application claims the benefit under 35 U.S.C. 119 of Canadian patent application serial no. 2,920,670 filed Feb. 12, 2016.

TECHNICAL FIELD

This document relates to shoulder braces and methods of use.

BACKGROUND

Clavicle braces have rigid straps that extend from a common point on a user's upper back and around the user's shoulders to restrict movement and promote healing of a broken clavicle. Shoulder braces employ springs to permit limited movement of the shoulders.

SUMMARY

A shoulder brace is disclosed comprising: a support structure; flat spiral torsion springs mounted to the support structure; and left and right shoulder straps each having a first strap part connected to the support structure and a second strap part connected to a free end of a respective spiral torsion spring.

A method is disclosed comprising: positioning a support structure against a user's upper back; looping left and right shoulder straps around a user's left and right shoulders, respectively; and in which each of the left and right shoulder straps connects to the support structure via a spiral torsion spring for applying tension through the respective left or right shoulder strap to pull the user's shoulders back.

A shoulder brace is disclosed comprising: left and right housings that are connected via a hinge and each mount a respective strap retractor; left and right shoulder straps each having a first strap part, connected to a respective one of the left and right housings, and a second strap part, connected to a respective strap retractor; and in which the left and right housings have a deployed position where the left and right housings spread apart from one another, and a folded position where the left and right housings stack one on top of the other.

A shoulder brace is disclosed comprising: a housing; strap retractors mounted within the housing; left and right shoulder straps each having a first strap part, a second strap part, and a torque adjuster, in each first strap is connected to the housing, each second strap part passes through a respective strap port in the housing to connect to a respective strap retractor, and each torque adjuster is between the first strap part and the second strap part for adjusting the length of the second strap part between the torque adjuster and the respective strap retractor; and in which the shoulder brace is configured to have a pre-torqued neutral position where each torque adjuster seats against the respective strap port and applies a non-zero tension to the respective strap retractor through the respective second strap part.

A shoulder brace is disclosed comprising: a support structure; strap retractors mounted to the support structure; left and right shoulder straps each having a first strap part connected to the support structure and a second strap part connected and wound within a respective strap retractor, in which each strap retractor is configured to extend fifteen inches or more of additional second strap part under increasing tension with increasing extension.

Shoulder posture correction devices are disclosed.

A shoulder brace is disclosed comprising: a support structure; a spiral torsion spring mounted to the support structure; and shoulder straps each having a first part connected to the support structure and a second part connected to a free end of the spiral torsion spring.

An upper back brace is disclosed with a support structure that sits flat on a user's upper back in use, and left and right shoulder straps that each loop over and under a respective shoulder of the user, with the left and right straps originating from, and terminating on, left and right housings, respectively, of the support structure, with each housing mounting a flat spiral torsional spring so that the rotational axis of the spring is directed into the user's back, with each flat spiral torsional spring being connected to an end of a respective strap, to provide a long-travel, free-wheeling strap retraction mechanism that pulls the respective shoulder backward and expands to accommodate movement of the user's shoulders as needed.

In various embodiments, there may be included any one or more of the following features: The support structure comprises left and right housings that are connected via a hinge and each mount a respective flat spiral torsion spring. The left and right housings comprise respective upper-back-contacting pads that cooperate in use to space the support structure and hinge out of contact with skin overlying a user's spine. The hinge comprises a left hinge and a right hinge, and the left and right housings are separated by a spacer part that connects to the left and right housings via the left hinge and the right hinge, respectively. The support structure has a clamshell design with a deployed position where the left and right housings are spread apart from one another, and a folded position where the left and right housings stack one on top of the other. Each of the left and right housings have an upper-back-contacting base and a top cover that collectively define an interior compartment mounting a respective flat spiral torsion spring. Each of the left and right housings further comprise a strap port, defined between the interior compartment and an exterior, through which the respective left or right shoulder strap passes. Each of the left and right housings further comprise a spool that is within the interior compartment and secured to the free end of the respective flat spiral torsion spring, the spool mounting the second strap part of the respective left or right shoulder strap. Each of the left and right housings comprise spool bearings that are located within the interior compartment. The spool bearings are located adjacent opposed first and second lateral walls, respectively, that define the strap port. Each of the left and right housings, the spool bearings are bushing sleeves positioned on respective posts. The spool bearings comprise one or more lateral projections. A torque adjuster between the first strap part and the second strap part for adjusting the length of the second strap part between the torque adjuster and the free end of the respective flat spiral torsion spring. The shoulder brace is configured to have a pre-torqued neutral position where each torque adjuster seats against a seating surface associated with a respective strap port to apply a non-zero tension to a respective flat spiral torsion spring through the respective second strap part. Each top cover is connected to a respective base via the hinge. Each of the left and right housings secure an anchor end of the respective flat spiral torsion spring. A coil axis of each flat spiral torsion spring is perpendicular to a contact plane defined by an upper-backcontacting surface of the support structure. For each of the left and right shoulder straps, the first strap part forms a padded shoulder loop and is wider than the second strap part. One or both of the left and right shoulder straps comprise a buckle and a length adjuster on the first strap part. The shoulder brace in combination with a user, or in position on a user. The spiral torsion springs comprise flat spiral torsion springs.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

Immaterial modifications may be made to the embodiments described here without departing from what is covered by the claims.

Figure 1:
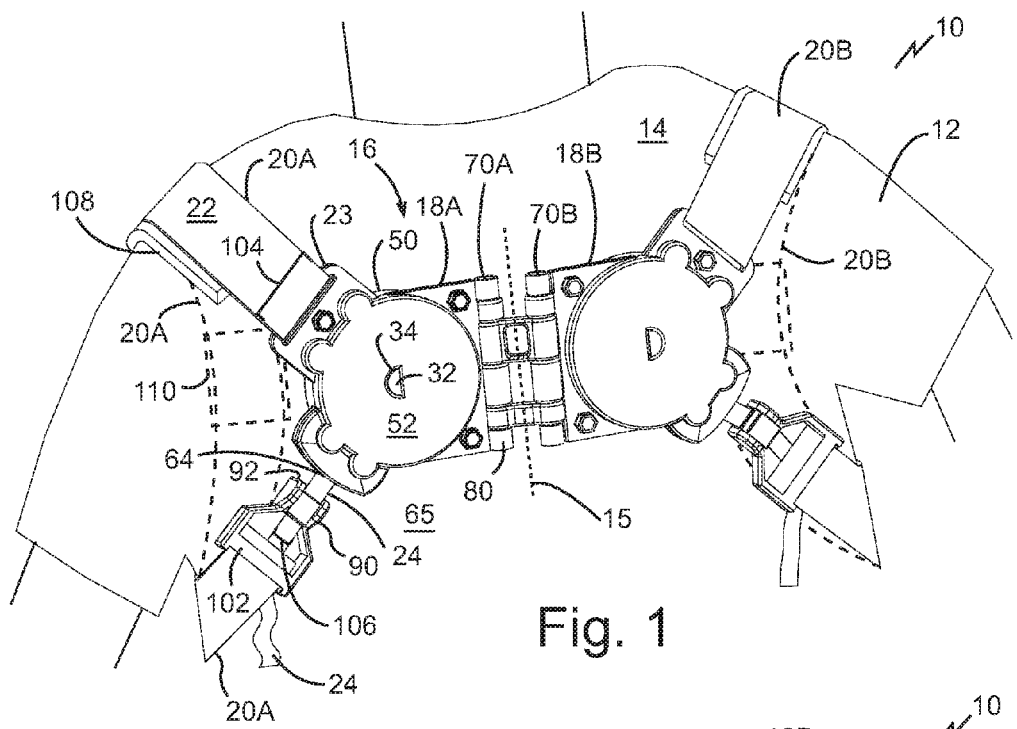
FIG. 1 is a perspective view of a shoulder brace in a deployed position in use on a user's back.
Figure 3:
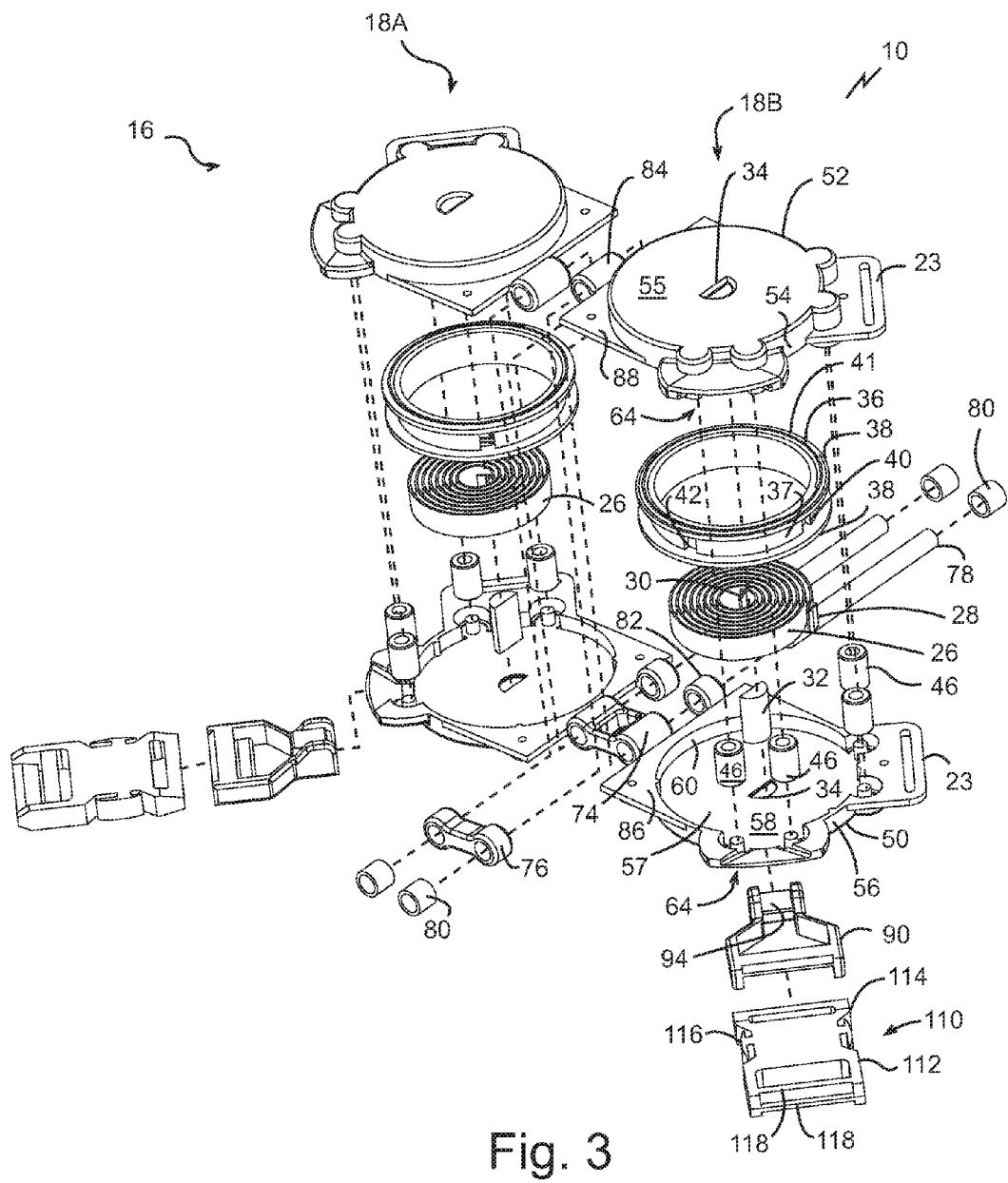
FIG. 3 is an exploded side perspective view of the shoulder brace in FIG. 1.
Figure 6:
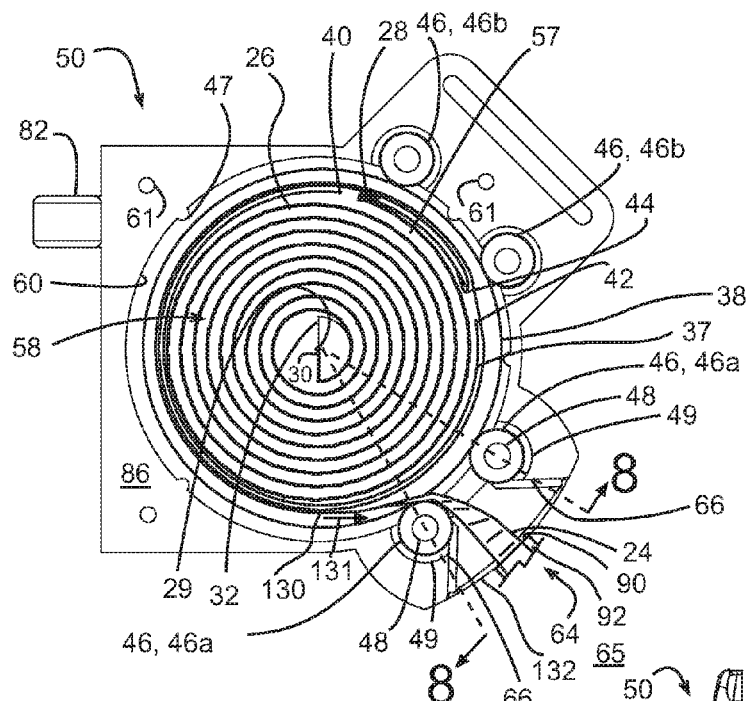
FIG. 6 is a top plan view of the base of the right housing depicted in FIG. 4 with a spiral torsion spring and a spool disc positioned in the interior compartment of the right housing.

Referring to FIG. 1, a shoulder brace 10 is illustrated having a support structure 16 and left and right shoulder straps 20A and 20B. Referring to FIG. 3, shoulder brace 10 may also comprise strap retractors, such as torsion springs mounted to support structure 16. One example of a torsion spring is a flat spiral torsion spring 26 as shown. Referring to FIG. 1, each of the left and right shoulder straps 20A, 20B may have a first strap part 22 and a second strap part 24. The first strap part 22 may be connected to the support structure 16, for example by mounting on spindle rod 23. Referring to FIG. 6, second strap part 24 may be connected to a free end 28 of a respective spiral torsion spring 26, for example by having free end 28 and second strap part 24 connected to a spool disc 36 as discussed further below.

Referring to FIG. 1, support structure 16 may comprise left and right housings 18A, 18B. Housings 18A, 18B may be connected via hinge, for example one or more hinges 70A and 70B. Referring to FIG. 6, each of the left and right housings 18A, 18B may mount a respective spiral torsion spring 26. Referring to FIG. 1, in use shoulder brace 10 may be secured to the upper back 14 of user 12 by looping the shoulder straps 20A and 20B around the respective shoulders of the user 12. After the brace 10 is in place, each spiral torsion spring 26 may pull the respective second strap part 24 towards the support structure 16 and provide tension in each shoulder straps 20A, 20B, and tension between the shoulder straps 20A, 20B. Such a configuration acts to pull the shoulders back and toward the spine 15 to provide posture correction for the user. Dual strap retractors mounted on the upper back will pull the shoulders back, in contrast with belt mounted straps that predominantly pull the shoulders down toward the waist.

Figure 2:
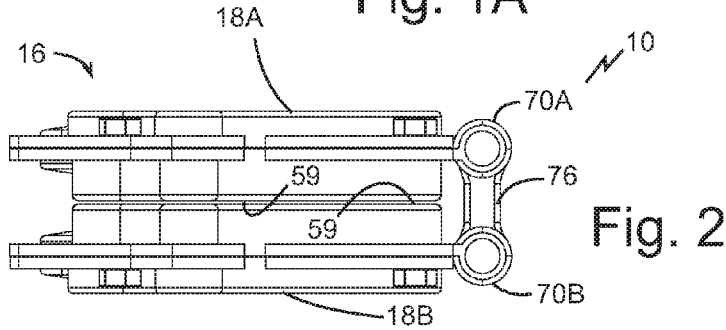
FIG. 2 is a side elevation view of the shoulder brace in FIG. 1 in a folded position.

Referring to FIG. 1, the first strap part 22 of each of the left and right shoulder straps 20A, 20B, may comprise a padded shoulder loop, with a removable or permanent under layer of padding 108 for comfortable contact with a user's skin or clothing. In some cases padding 108 is integral to first strap part 22. First strap part 22 may have a width 104 greater than a width 106 of second strap part 24. The width of each strap part may refer to a lateral width perpendicular to an axis of each strap. One or both of the left and right shoulder straps 20A, 20B may comprise a buckle 110 on the first strap part 22, for quick disconnection and connection of the strap. Referring to FIG. 2, a length adjuster, such as spindle rods 118 on buckle 110 may be present on the first strap part 22 (not shown) for fitting the strap to the dimensions of a particular user. Referring to FIGS. 1 and 2, shoulder brace 10 may comprise spindle rod 23 on support structure 16 used for securing first strap part 24 to the support structure 16. Other suitable length adjusting mechanisms may be used.

Figure 1A:
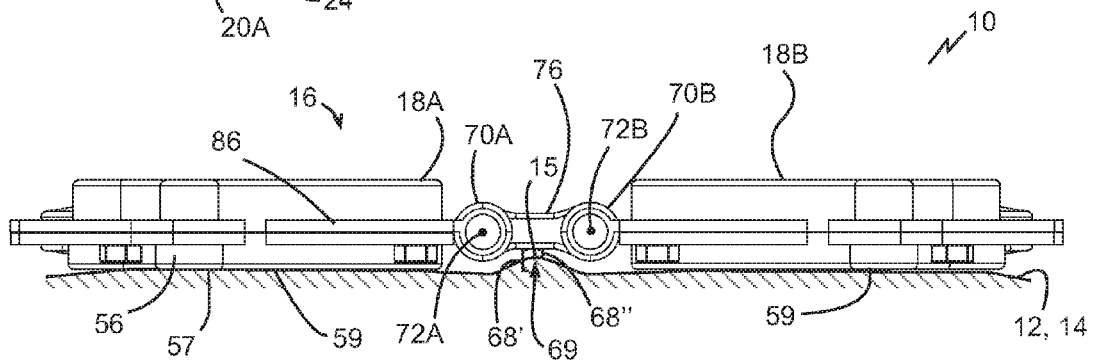
FIG. 1A is side elevation partial section view of the shoulder brace in FIG. 1 positioned on a user's back.

Referring to FIGS. 1A and 2, the hinge between housings 18A and 18B may comprise a left hinge 70A and a right hinge 70B. Left and right housings 18A, 18B may be separated by a spacer part 76 that connects to the left and right housings 18A, 18B via the left hinge 70A and the right hinge 70B, respectively. The use of spacer part 76 and housings 18A, 18B, is one example of an articulating hinge, and may provide a butterfly appearance. In one embodiment, support structure 16 has a clamshell design with a deployed position where the left and right housings 18A, 18B are spread apart from one another (FIG. 1A), and a folded position where the left and right housings 18A, 18B are stacked one on top of the other (FIG. 2) as if the housings 18 were pages in a booklet. The folded position is achieved in the example by rotating housings 18A and 18B along right and left hinge axes 72A and 72B, respectively, until upper-back-contacting surfaces 59 of each housing 18A, 18B meet as shown. The folded position provides a compact, low profile configuration for storage and packaging. In addition, the hinged connection between the housings 18A, 18B permit housings 18A, 18B to pivot in step with the natural movements of the upper back for increased comfort during use, with such back movements often caused by movements of the user's shoulder blades (not shown), which may cause the part of the upper back shown in FIG. 1A to assume concave, convex, flat, and other positions.

Referring to FIG. 1A, left and right housings 18A and 18B, may comprise respective upper-back-contacting pads, for example defining upper-back-contacting surfaces 59. The upper-back-contacting pads may cooperate in use to space the support structure 16 and hinge 70 out of contact with skin overlying a user's spine 15. The pads may be integral to support structure 16, or may be mounted to an underside of the support structure (not shown). In the example shown, each pad is integrally formed by base plate 57 and sidewalls 56. Sidewalls 56 project each base plate 57 toward the upper back and away from a mating flange 86 of base 50, the mating flange 86 defining a plane that overlaps the respective hinge axis 72.

Figure 16:
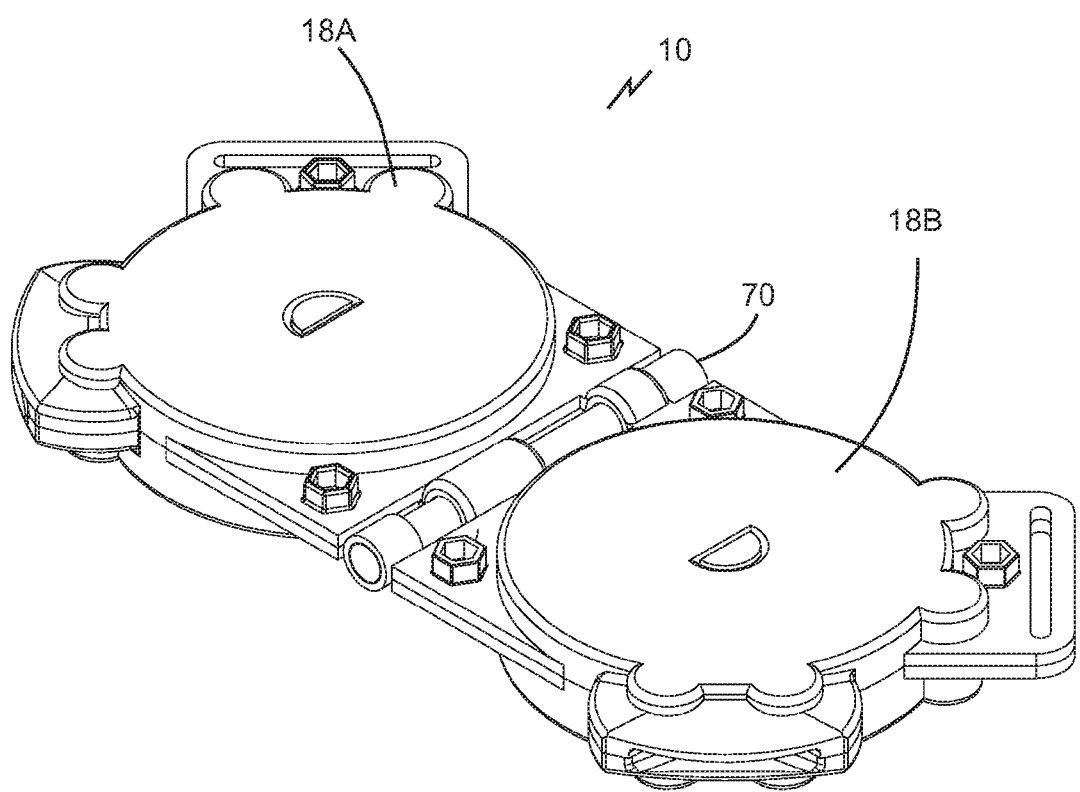
FIG. 16 is a perspective view of a further embodiment of a shoulder brace with a single hinge.
Figure 17:
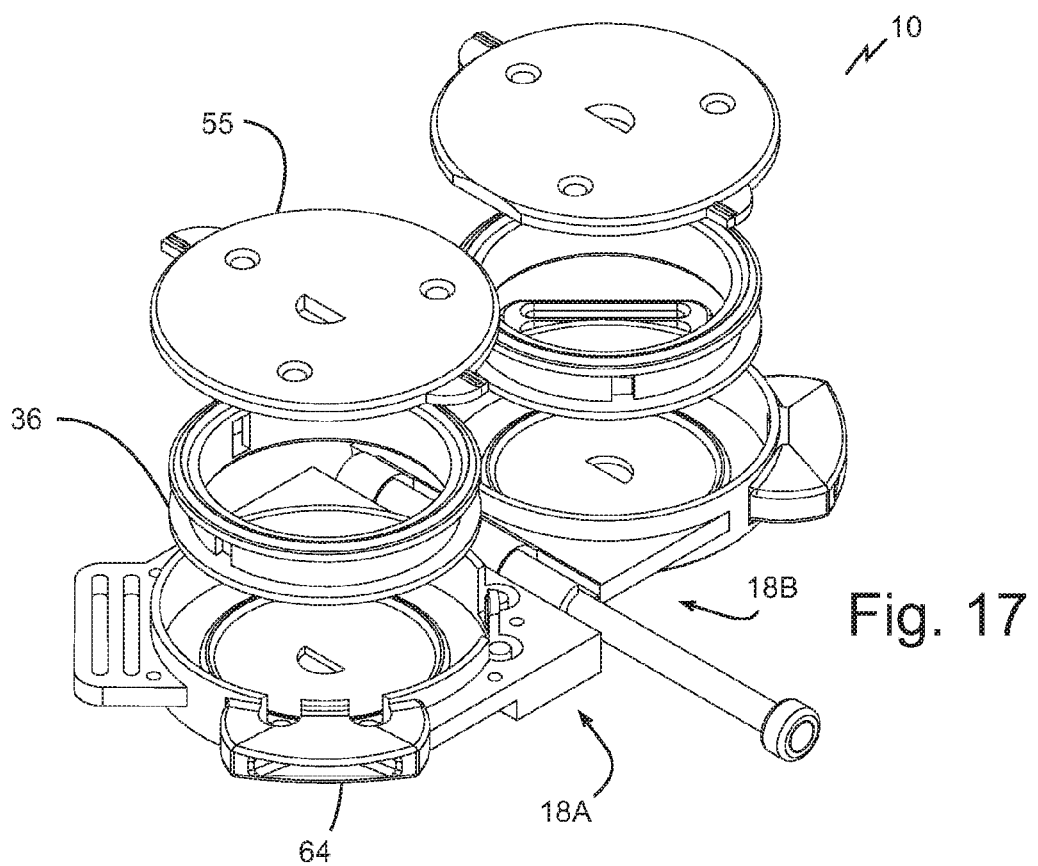
FIGS. 17-18 are exploded perspective views of a further embodiment of a shoulder brace.
Figure 18:
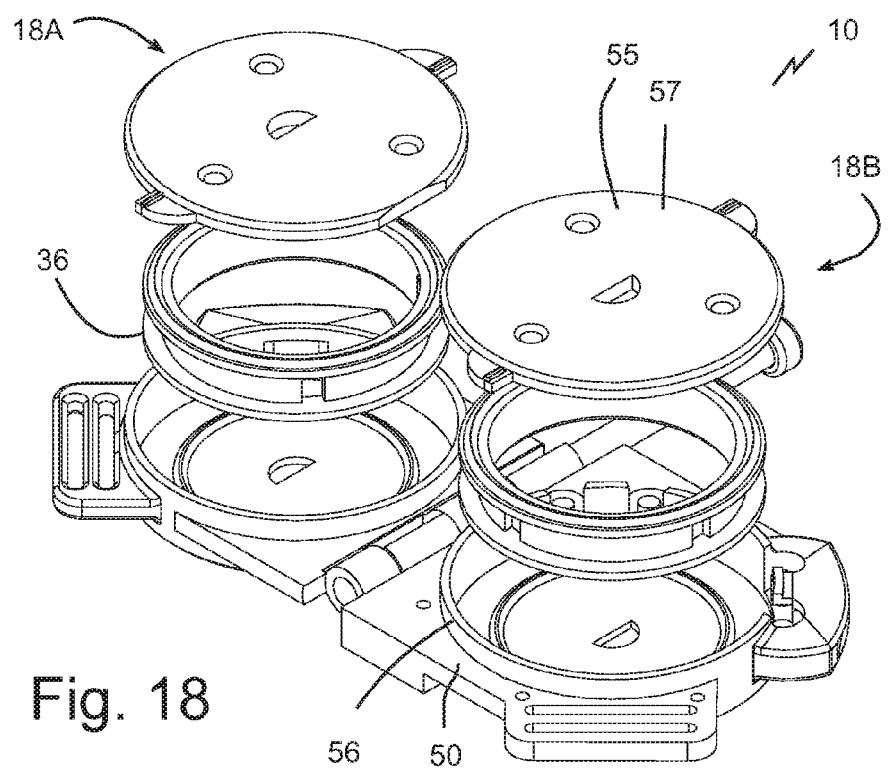

The upper-back-facing surfaces of the hinge, such as hinges 70A, 70B, and spacer part 76 (if present), may define a spine-receiving recess 69 from spacer part 76 to a plane (not shown) defined by upper-back-contacting surfaces 59, the recess 69 having a depth 68'. In use the depth 68' may be selected to provide a non-zero distance 68" between the skin overlying a user's spine 15 and the upper-back-facing surfaces of the hinge and spacer part 76 (if present), to avoid contact between the part of the user's skin that overlies the spine 15 and the support structure 16 in use. In some cases the non-zero distance 68" may be maintained in convex and concave back positions (shoulders pulled forward and back, respectively). By spacing the hinge or hinges from the user's upper back, comfort is increased because friction between the skin overlying the spine 15 and the support structure is reduced or avoided. Having two springs 26 separated by a hinge 70 allows the support structure 16 to contour to the body as the straps 20 get pulled in different directions. A hinged structure makes the device more comfortable than a flat rigid piece of plastic with no flexibility. As shown, the hinge or space part 76 may overlie the spine 15 in use, such that a spine axis runs parallel to hinge axes 72A, 72B as shown. Referring to FIGS. 16-18 embodiments are shown with a single hinge 70, and in such examples the hinge 70 may overlie the spine 15 but be spaced to avoid contact with the skin overlying the spine 15.

Referring to FIG. 3, each of the left and right housings 18A, 18B may have an upper-back-contacting base 50 and a top cover 52 that collectively define an interior compartment 58. Referring to FIG. 6, each interior compartment 58 may mount a respective spiral torsion spring 26, for example such that a coil axis 29 of spring 26 is perpendicular to a contact plane (understood to be defined by the plane of the page in the view shown) defined by upper-back-contacting surface 59 of the support structure 16. Each interior compartment 58 and flat spiral torsion spring 26 may thus define a low profile, compact unit for discreet use on a user's back, while permitting relatively long strap travel.

Referring to FIGS. 1, 1A, and 3, each top cover 52 may be connected to a respective base 50 via a hinge, for example a respective hinge 70A or 70B. Thus, each housing 18 may be accessed, for example to replace a spring 26 or other interior component, by unlocking or unbolting the base 50 and cover 52, and rotating the cover 52 relative the base 50 in a clamshell fashion to an open position (not shown). In other cases the cover 52 and base 50 may be hinged at a location other than as defined by hinges 70. The use of clamshell housings 18A, 18B, provides a dual clamshell appearance and functionality.

Referring to FIGS. 1 and 6, in one embodiment, each of the left and right housings 18A, 18B comprise a strap port 64, defined between the interior compartment 58 and an exterior 65, through which the second strap part 24 passes to access the spring 26. The strap port 64 may be collectively defined by base 50 and top cover 52, or by one of them.

Figure 10:
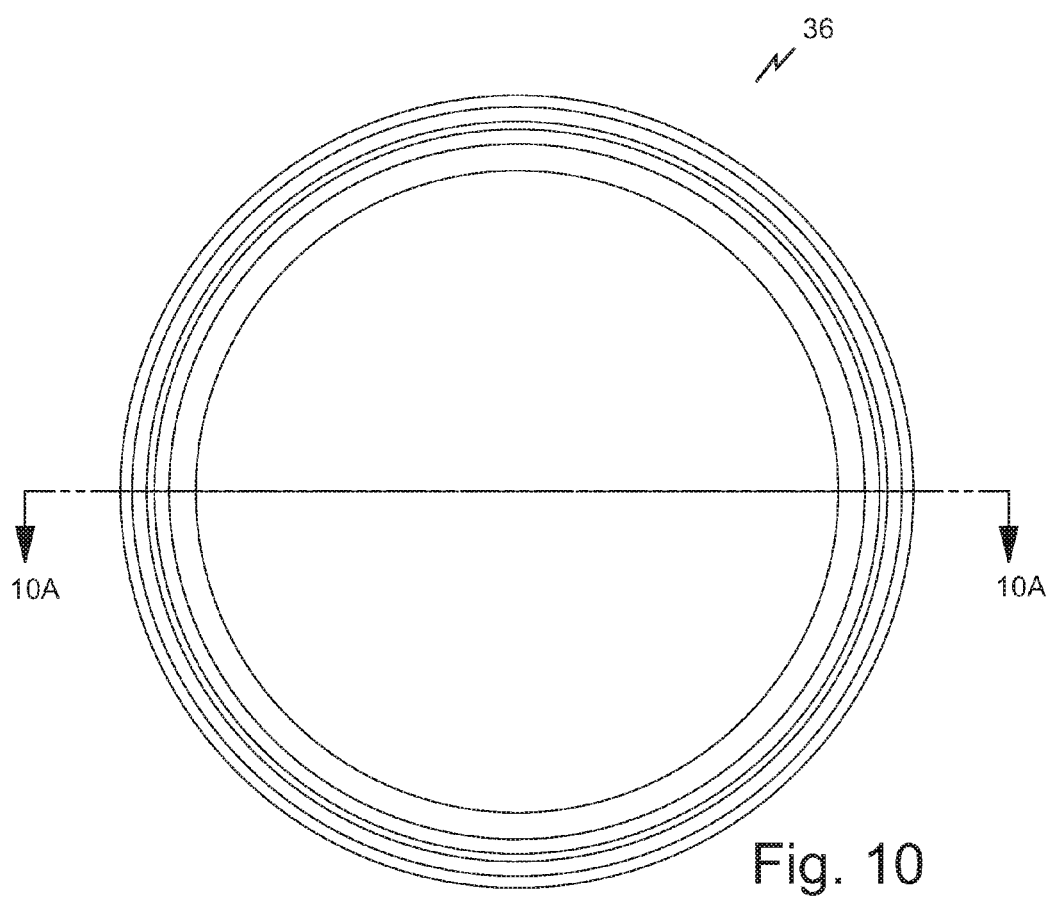
FIG. 10 is a top plan view of a spool disc used in the shoulder brace of FIG. 3.
Figure 10A:
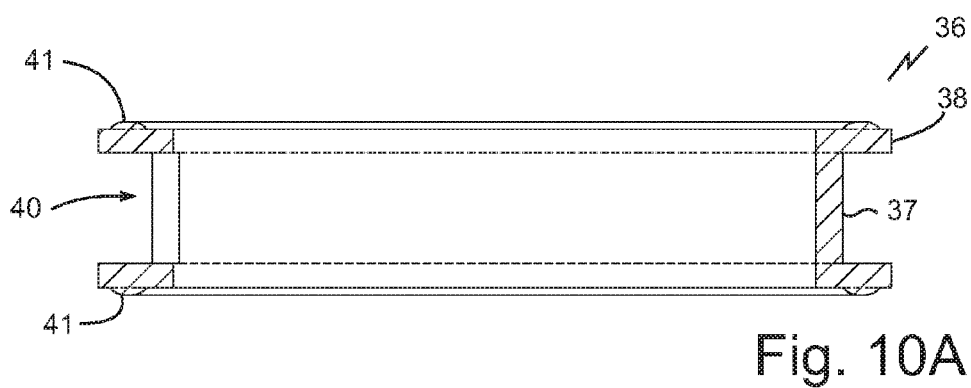
FIG. 10A is a section view taken along section lines 10A in FIG. 10.

Referring to FIGS. 3 and 6, each of the left and right housings 18A, 18B may further comprise a spool, such as a spool disc 36. Referring to FIG. 6, spool disc 36 may be located within the interior compartment 58. Spool 36 may mount the second strap part 24 of the respective left or right shoulder strap 20A, 20B. Referring to FIGS. 10 and 10A, an embodiment of spool 36 is depicted. Referring to FIGS. 3 and 6, spool 36 may comprise a cylindrical spool body 37 separating opposed flanged ends 38. Spool 36, bushing 46, or other parts, may be made of a suitable material such as TEFLON™.

Referring to FIG. 6, spool disc 36 may be secured to the free end 28 of the respective spiral torsion spring 26. For example spool 36 defines an opening 40, such as a radial opening between exterior and interior surfaces of body 37 as shown, through cylindrical spool body 37, and free end 28 may be bent around and under the opening 40. Free end 28 may be secured via a suitable mechanism such as adhesive, fasteners, or friction fit.

Spool 36 may be used to mount the second strap part 24. Referring to FIG. 6, spool 36, for example cylindrical spool body 37 may define an opening 42, such as a radial opening as shown, for mounting the spring end 44 of second strap part 24. For example strap part 24 may wrap circumferentially around the spool body 37 part of a full rotation, or one or more rotations, and end 44 may pass through opening 42 and be secured to an interior surface or underside of the spool body 37. By mounting the spool disc 36 to the free end 28 of spring 26, and mounting the second strap part 24 to the spool disc 36, the spool 36 is permitted to float in the interior compartment 58, while rotating in response to torque exerted upon the spool 36 by the spring 26 and the second strap part 24.

Various suitable bearing mechanisms may be used to facilitate the rotation of spool 36 on the support structure. Referring to FIG. 6, each of the left and right housings 18A, 18B may comprise one or more spool bearings 46 that are located within the interior compartment 58. Spool bearings 46a may be adjacent opposed first and second lateral walls 66, respectively, that define the strap port 64. Bearings 46a, or other bearing devices may act as bearings for the second strap part 24 as shown. An example of spool bearings 46 are bushing sleeves mounted on posts 48, whose axes are parallel to coil axis 29.

One or more other spool bearings, such as bearings 46b, may be positioned at various other positions around an interior-facing cylindrical side wall surface of the housing 18, for example one or both surfaces 60 and 62 (of base 50 and top cover 52, respectively), which may individually or collectively (as shown) define indented recesses 49, 51, respectively, that mount bushings 46 and posts 48. In FIG. 6 the second strap part 24 wraps clockwise toward end 44, and contacts spool 36 at a point 130, which defines a force vector along tangent line 131 when under a torque that tends to pull second strap part 24 out of the housing 18. Such a torque will act to pull the spool 36 in the direction of the line 131, in some cases distorting the spool 36 and spring 26 into an oblique shape, and one or more bearings 46b may be positioned on parts of surfaces 60 and/or 62 that face into the direction of the line 131 as shown. For example, bearings 46a and 46b may be positioned on only one semi-circular side, in this case the right side, of the housing 18 in the Figure, the interior compartment 18 divided into two semi-circular sides by a plane (not shown) that runs perpendicular to line 131 at point 130. Spool bearings 46 may rotate on shafts or posts 48, and minimize contact points, and hence friction, of the spool 36 within the housing 18.

Figure 7:
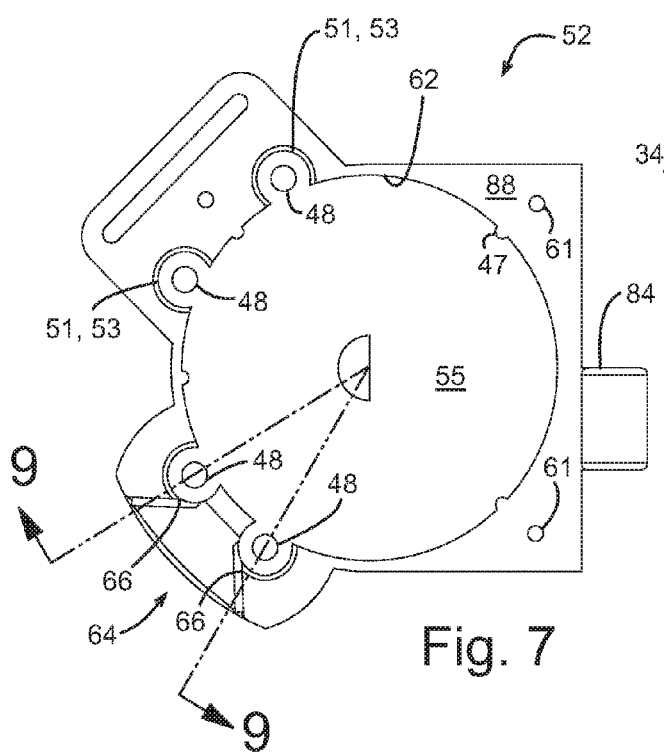
FIG. 7 is a bottom plan view of the top cover of the left housing depicted in FIG. 1.
Figures 8, 9:
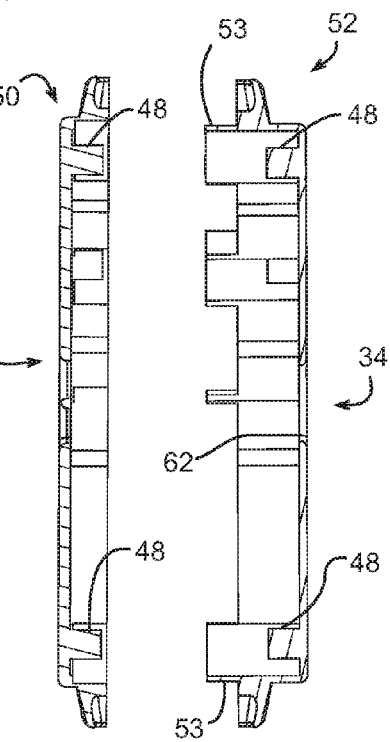
FIG. 8 is a section view taken along section lines 8 in FIG. 6, with the spiral torsion spring and second strap part removed.
FIG. 9 is a section view taken along section lines 9 in FIG. 7.

In some cases the spool bearings comprise one or more lateral projections. Referring to FIGS. 6 and 7, for example base 50 may define lateral bearing projections, such as bumpers 47, for contacting and positioning spool 36 in use. Referring to FIG. 9, top cover 52 may comprise axial cups or projections 53 depending from surface 62 into the recesses 49 of base plate 57, within which the respective bushings 46 may be positioned. In another case base plate 57 may mount, and top cover 52 may receive, such projections 53. The spool 36 itself may carry one or more bearing mechanisms, such as lateral or axial projections that extend toward the walls of interior compartment 18. Referring to FIG. 10A, spool 36 may have axial-facing bearing surfaces 41, for example a ring that extends in an axial direction out of flange 38, for contacting a suitable bearing mechanism or plates 55 and 57 (FIG. 6). The flanges 38 may act as lateral projections that bear against the inner walls of the interior compartment 18.

Referring to FIGS. 3 and 6, each of the left and right housings 18A and 18B may secure an anchor end 30 of the respective flat spiral torsion spring 26. Housings 18A and 18B may comprise a dowel or arbor 32 that provides an anchoring point for the anchor end 30 of spiral torsion spring 26. In the example shown the arbor 32 has a semi-circular cross-sectional shape that provides a mounting point for anchor end 30 to bend around and secure to. Referring to FIG. 3, arbor 32 may be positioned within openings 34 defined by the top cover 52 and base 50 of housings 18A and 18B. Referring to FIG. 6, each flat spiral torsion spring 26 may be configured to have a coil axis 29 perpendicular to a contact plane defined by an upper-back-contacting surface 59 of the support structure, such plane understood to be parallel to the plane of the page in FIG. 6. In such an embodiment the flat spiral torsion spring 26 and housing 18 effectively form a disc that sits flat side against a user's back, whilst still permitting long-travel retraction of strap 20.

Figure 4:
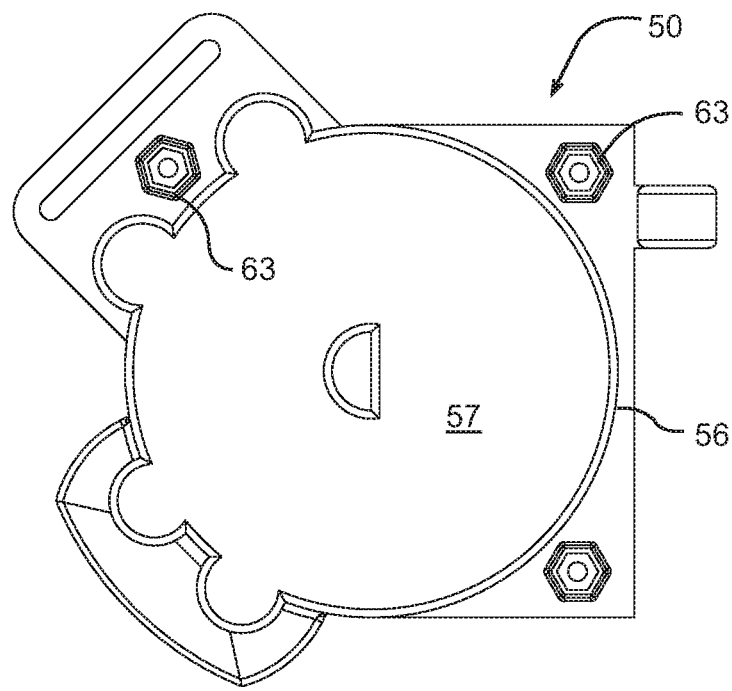
FIG. 4 is a bottom plan view of the base of the right housing of the shoulder brace in FIG. 1.
Figure 5:
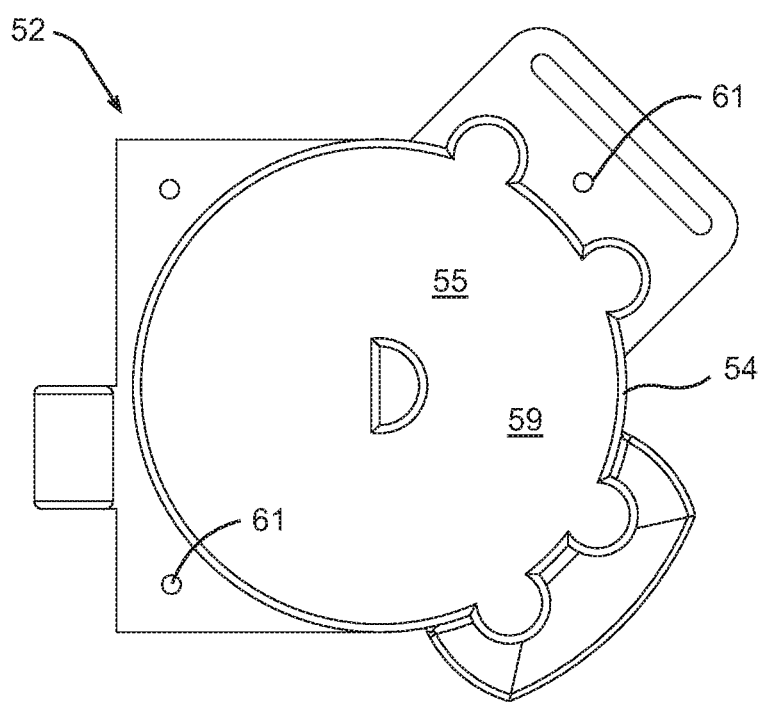
FIG. 5 is a top plan view of the top cover of the right housing shown in FIG. 1.

Referring to FIGS. 4 and 6, base 50 may comprise a base plate 57. Base plate 57 may define an interior side wall 56. Referring to FIG. 7, the top cover of housings 18 may define a top plate 55. Top plate 55 may define an interior side wall surface 62. Referring to FIGS. 4 and 6, base 50 may comprise fastener openings, such as nut or bolt sockets 63, for securing the base to the top cover 52. Referring to FIG. 5, top cover 52 may comprise a top plate 55. Top plate 55 may define side walls 54. Top plate 55 may define fastening openings, such as bolt holes 61, for receiving fasteners (not shown) passed through respective aligned holes 61 from base plate 57.

Referring to FIGS. 3, 6, and 7, base 50 and top cover 52 may comprise mating flanges 86 and 88. Flanges 86, 88 may extend laterally from side wall surfaces 60, 62, respectively. Flanges 86, 88 may also define fastener holes 61. Each flange 86, 88 may have a rectangular shape shown with spindle rod 23 and strap port 64 defined at corners of one side edge of the rectangle, and the hinges 70 defined along the opposing side edge of the rectangle. Strap port 64 and spindle rod 23 may be positioned at suitable angles, for example one-hundred-thirty-five degrees, relative to adjacent side edges.

Figure 11:
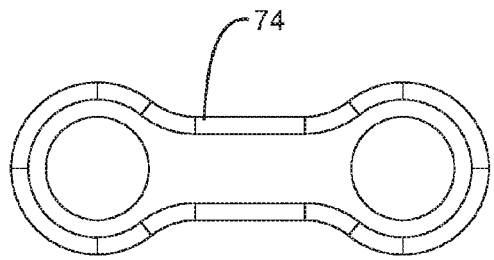
FIG. 11 is a top plan view of a first dual hinge spacer part.
Figure 12:
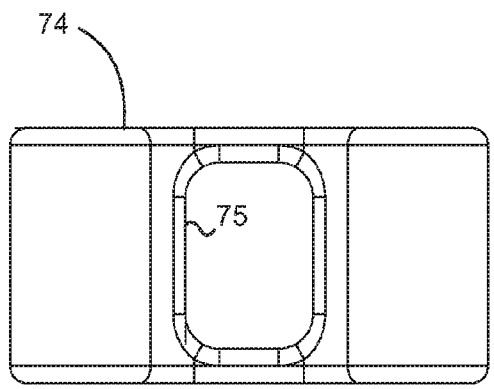
FIG. 12 is a side elevation view of the first dual hinge spacer part depicted in FIG. 11.
Figure 13:
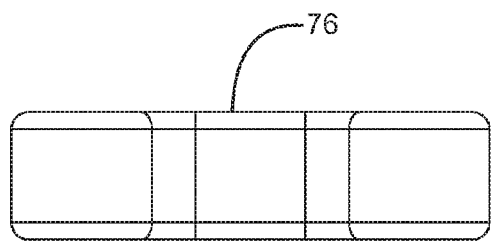
FIG. 13 is a side elevation view of a second dual hinge spacer part.

Referring to FIG. 3, for each housing 18, hinge 70 may be made up of respective hinge rings 82, 84, an axle rod 78, axle rod nuts or caps 80, a first dual hinge spacer part 74, and a second spacer part 76. Other mechanisms of providing hinges 70, 70A, and 70B may be used. Referring to FIG. 11, one embodiment of the first dual hinge spacer part 74 is illustrated. Referring to FIG. 12, the first space part 74 may define a cut out section 75. Referring to FIG. 13, an embodiment of the second dual hinge spacer part 76 is illustrated.

Referring to FIG. 1, shoulder brace 10 may comprise a torque adjuster 90 between the first strap part 22 and the second strap part 24. Adjuster 90 may act as a length adjuster to adjust the length of the second strap part 24, and in some cases adjuster 90 may act to pre-torque the strap 20. Referring to FIGS. 1 and 6, the length of the second strap part 24 may be defined between the torque adjuster 90 and the free end 28 of the respective spiral torsion spring 26. Torque adjuster 90, which may be a clip, may be used to facilitate pre-torqueing of the strap to permit a user to adjust the tension in the strap 20 and to increase the torque required to move the shoulders and extend the strap 20 during use.

Referring to FIG. 6 shoulder brace 10 may be configured to have a pre-torqued neutral position where a respective torque adjuster 90 seats against a respective seating surface 132 adjacent or lining strap port 64. The torque adjuster 90 may be adjusted, for example by reducing the length of the second strap part 24, to apply a non-zero tension to a respective spiral torsion spring 26 through the second strap part 24 when in a neutral position. Thus, by shortening the second strap part 24 between adjuster 90 and free end 28, and then restricting full retraction, in the neutral position shown, of the second strap part 24 into the housing 18, the spring 26 becomes loaded when in neutral, and the initial torque required to extend the strap 20 out of strap port 64, and the resulting torque to continue extension past initial, is increased. The neutral position is understood to mean the position the strap 20 assumes when the strap 20 is under no external tension from a user, for example when the brace 10 is not assembled on a user.

Figure 14:
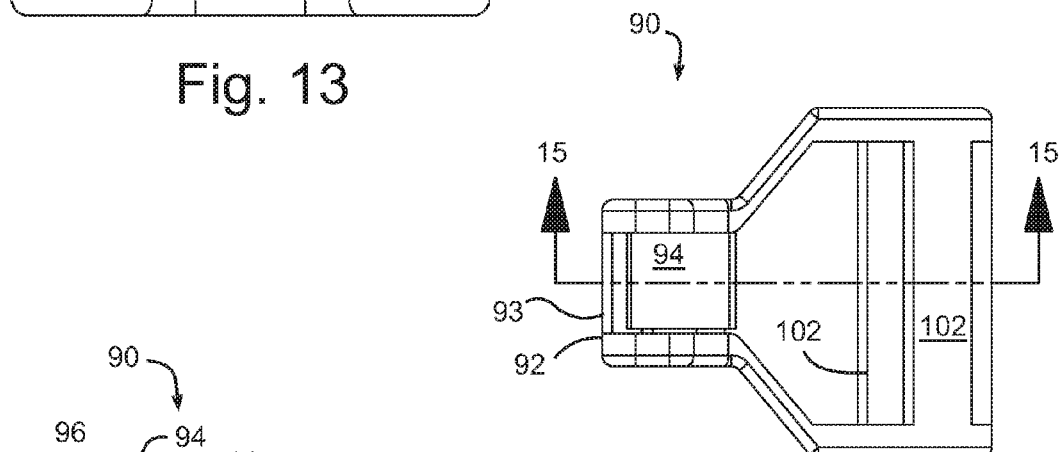
FIG. 14 is a top plan view of a torque adjuster clip shown in FIG. 1.

Referring to FIG. 14, one embodiment of the torque adjuster 90 is illustrated. Referring to FIGS. 1 and 14, torque adjuster 90 may achieve one or both of the following functions. One, adjuster 90 may permit pre-torqueing as described above. Two, adjuster 90 may act as a reducer to transition the strap 20 from a relatively thin second strap part 24 to the relatively wide first strap part 22 while minimizing the length of second strap part 24 that contacts or lies against the user's skin or clothing in use. The thinner second strap part 24 may be a cable, or may have the thickness of a cable in some cases, and such may otherwise be uncomfortable if resting under tension directly over a user's skin for long periods of time.

Figure 15:
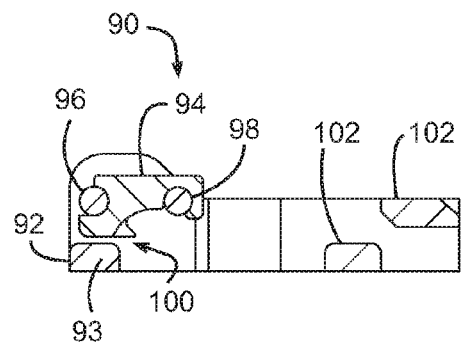
FIG. 15 is a section view taken along section lines 15 in FIG. 14.
Figure 19:
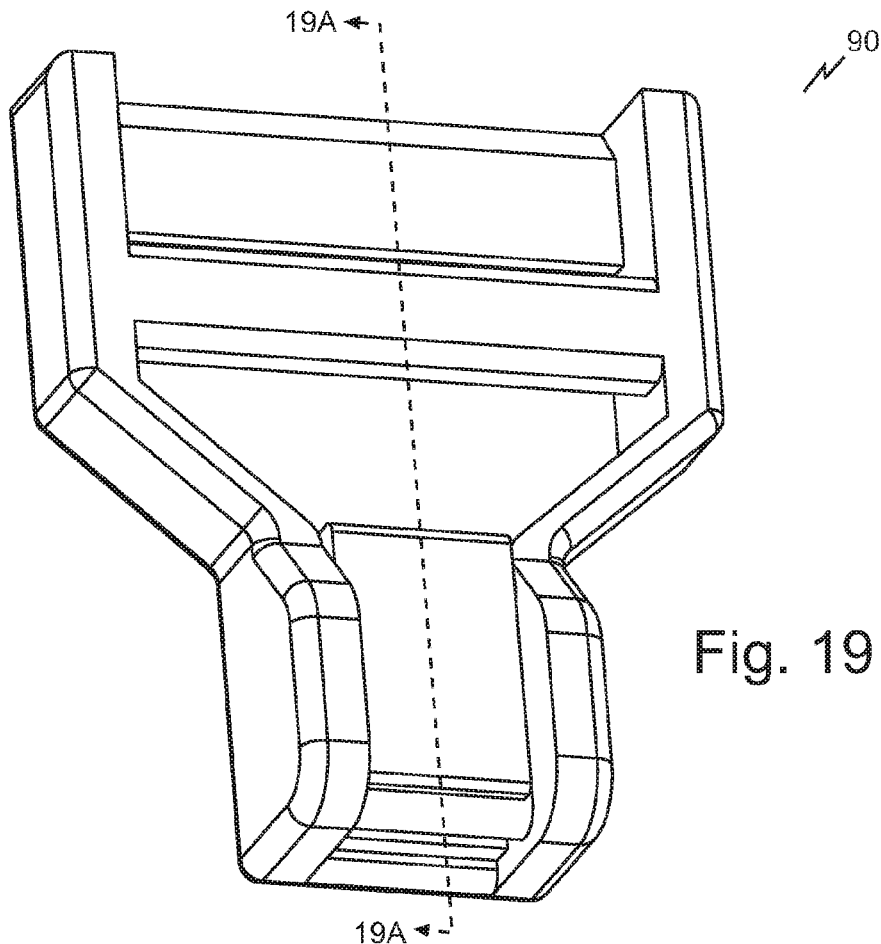
FIG. 19 is a perspective view of a further embodiment of a torque adjuster clip.
Figure 19A:
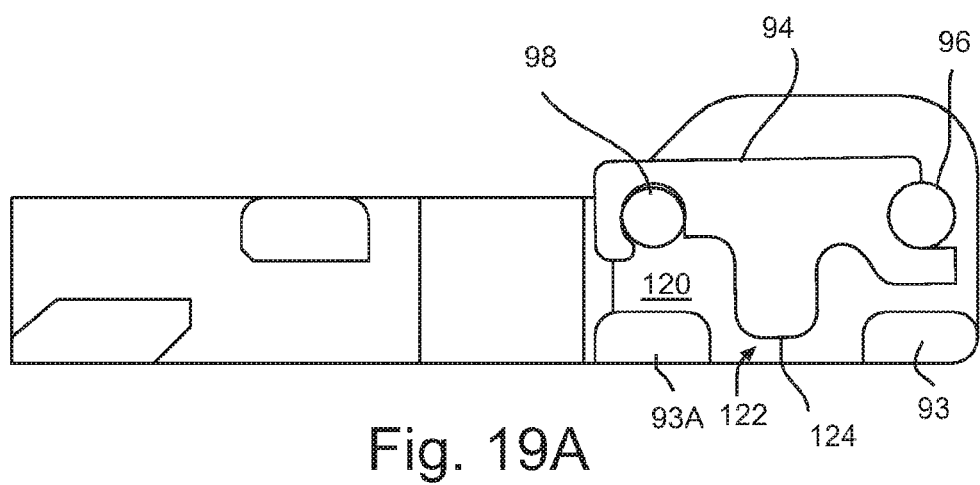
FIG. 19A is a section view taken along section lines 19A in FIG. 19.

Referring to FIGS. 1, 14, and 15, adjuster 90 may comprise a suitable mechanism for retaining the second strap part 24 at a desired length, for example via a cam lock lever 94 for locking the torque adjuster 90 in place along the second strap part 24. Referring to FIG. 1, torque adjuster 90 may comprise spindle rods 102 used to mount, and in some cases adjust the length of, the first strap part 22 and bridge the first and second strap parts 22 and 24, respectively. Referring to FIG. 15, torque adjuster 90 may comprise a pivot pin 96 that permits the rotation of cam lock lever 94 to unlock and lock cam lock lever 94 by engaging locking pin 98, to grip a second strap part 24 (not shown) positioned within a strap passage 100 between lever 94 and strap gripping bar 93. Referring to FIGS. 19 and 19A, a further embodiment of a torque adjuster clip 90 is illustrated. Referring to FIG. 19A, torque adjuster 90 may define a strap passage 120 for passing and securing the second strap part (not pictured). Passage 120 may be defined in use between cam lever 94 and strap gripping bars 93, 93A. A male part 124, such as a tongue, may extend from cam lever 94 toward or into a channel or gap 122 between bars 93, 93A to pinch the strap part securely between bars 93, 93A.

Referring to FIG. 1, first strap part 22 may comprise a length adjuster such as a buckle 110. One or both straps 20 may have buckles. Referring to FIG. 3, buckle 110 may comprise male part 112 and female part 114 that separate when release buttons 116 are squeezed simultaneously. Buckle 110 may also comprise spindle rod 118 for adjusting the length of first strap part 22. Torque adjuster 90 and buckle 110 may be modified to increase comfort for the user, for example by use of contact pads (not pictured). A quick release device, such as certain types of buckles including the one shown, may be used to help the user get out of the device safely.

Referring to FIG. 1, a method of use may comprise positioning support structure 16 against a user's upper back 14. Left and right shoulder straps 20A, 20B may be looped around a user's left and right shoulders, respectively. Each of the left and right shoulder straps 20A, 20B may connect to the support structure 16 via a strap retractor or spiral torsion spring 26 for applying tension through the respective left or right shoulder strap 20A, 20B to pull the user's shoulders back. In one case, a user adjusts the length of the straps 20 prior to fitting the brace 10 on. In another case the user adjusts the strap length while the brace 10 is on. In one case the user fits one shoulder loop over one shoulder, and then wraps the first and second strap parts, which are disconnected, around the second shoulder, and connects the strap parts to assemble the device on the user. In other cases the torque adjuster 90 may be set, during use or before fitting the brace 10 on the user, to pre-torque the brace 10 to provide for more resistance against movement. For example, a user recovering from a clavicle injury may initially desire almost full movement restriction, and as the injury heals, the torque adjuster may be adjusted to gradually reduce the pre-torqueing to permit greater and greater range of movement.

Referring to FIG. 16, a further embodiment of shoulder brace 10 is illustrated. Shoulder brace 10 may comprise a single hinge 70 used to space the left and right housings 18A, 18B. Referring to FIGS. 17 and 18, a further embodiment is shown where top cover 52 comprises a top plate 55, and side walls 56 of base 50 extend to mount top plate 55. Plate 55 may comprise lateral projections 120, such as handles or tabs, that lock in corresponding receivers (not shown) to secure the cover 52 in place. Strap ports 64 are shown as being defined entirely by base 50.

Figure 20:
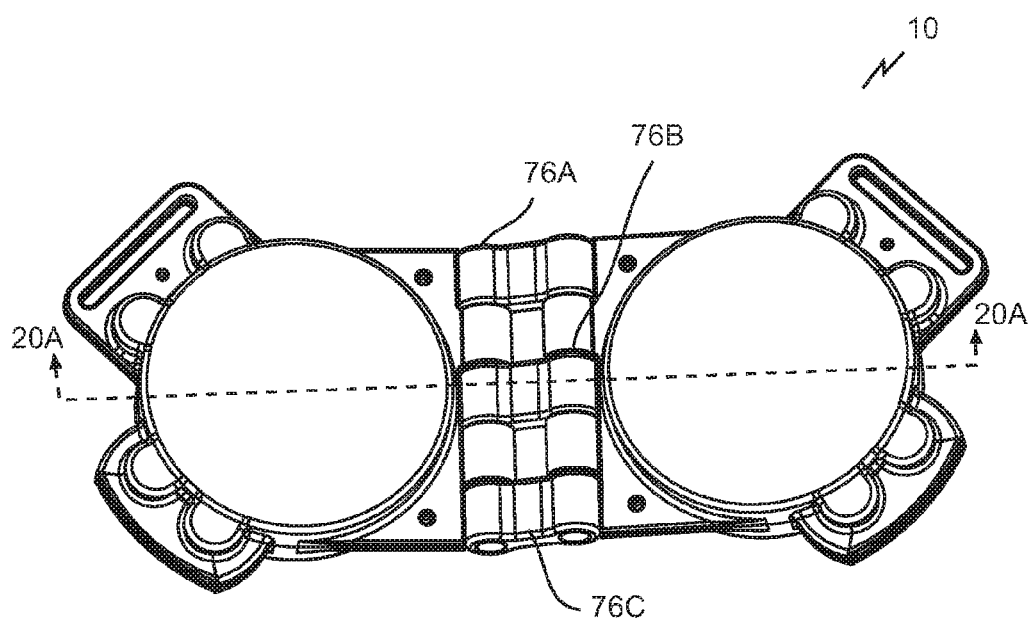
FIG. 20 is a perspective view of a further embodiment of a shoulder brace with a hinge comprising three spacer parts.
Figure 20A:
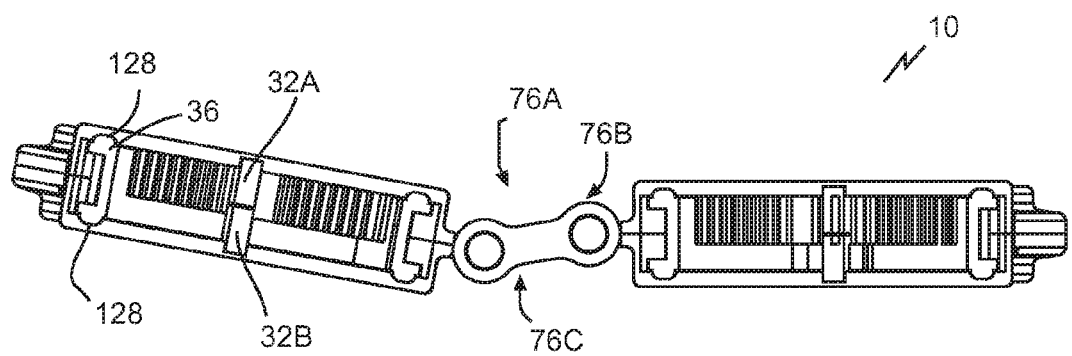
FIG. 20A is a section view taken along section lines 20A in FIG. 20.
Figure 21:
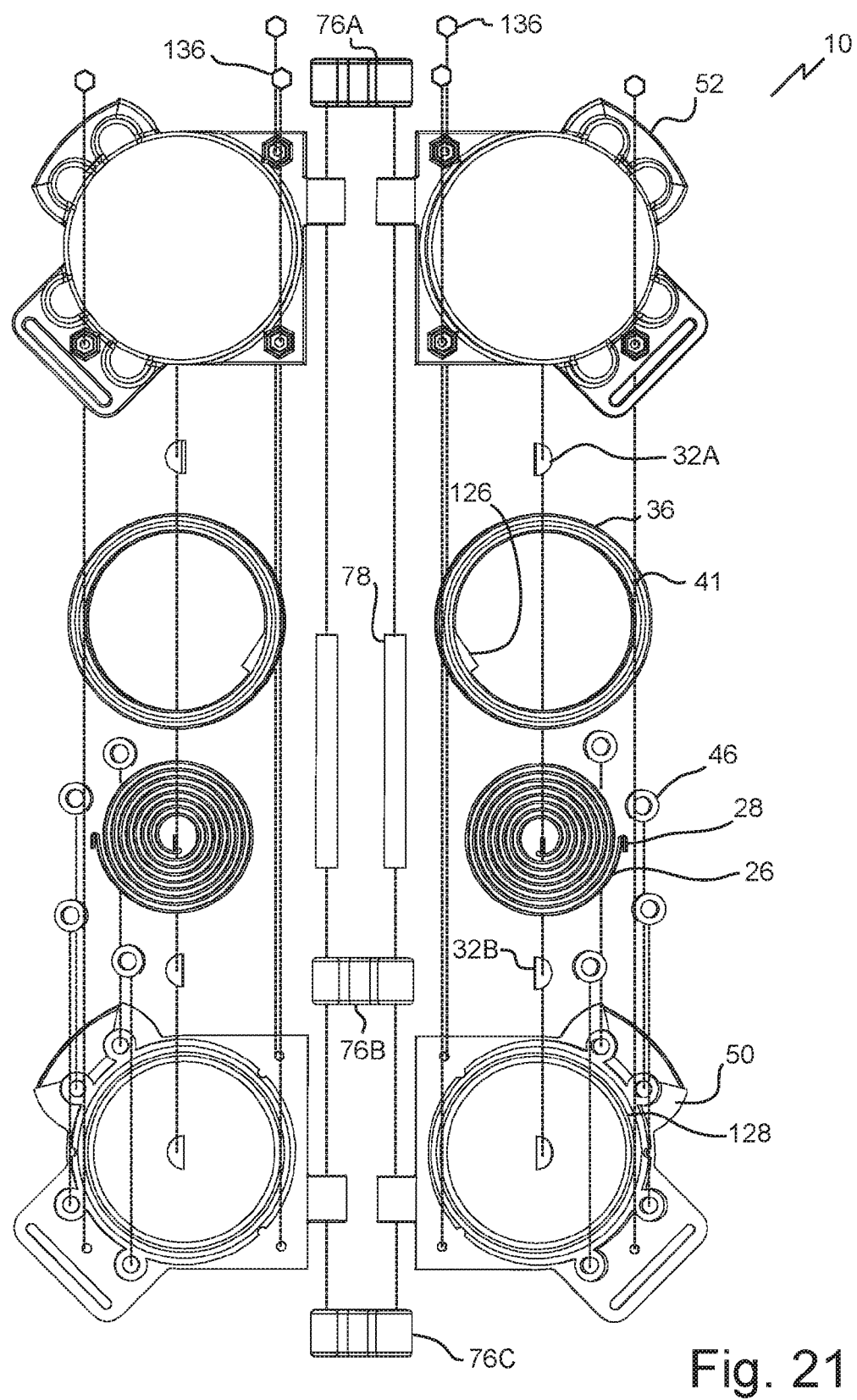
FIG. 21 is an exploded top plan view of the shoulder brace of FIG. 20.

Referring to FIGS. 20-21, a further embodiment of a shoulder brace 10 is illustrated. Shoulder brace 10 may have a hinge comprising three or more dual hinge spacer parts 76A, 76B and 76C. Spacer parts 76A, 76B, and 76C may cooperate to receive dual axle rods 78 as shown to secure each half of the device together. Referring to FIGS. 20A and 21, the top cover 52 and base 50, or one of them, may define a circumferential groove 128 for aligning the spool 36 in the brace 10, for example by being shaped to receive corresponding circumferential bearing projections or surfaces 41 on the top and bottom faces of the spool 36. A ring bearing or other suitable bearing, such as a thrust bearing, may be mounted in groove 41. Each arbor 32 may be formed by two or more parts, such as arbor halves 32A and 32B as shown, which fit within corresponding recesses or thru-passages in the cover 52 and base 50. Referring to FIG. 21, spool 36 may comprise a part 126, such as a shoulder or fin, defined or otherwise connected to an inner surface of the spool 36 for mounting, such as by hooking, the free end 28 of the spring 26. Other mechanisms of mounting the spring to the spool without passing the spring through to the exterior surfaces of the spool may be used. Top cover 52 and base 50 may be secured to each other by a suitable mechanism, such as using fasteners such as a plurality of bolts 136 with or without nuts, or using a locking system such as a tonge and groove, ship lap joint, a friction fit, a snap fit, a slot and lip fit, or using an adhesive such as glue, or using one or more of the foregoing or other mechanisms to secure the two parts together.

A torsion spring is a type of spring that stores mechanical energy when a twisting force (torsion) is applied. A spiral torsion spring has a coil portion with one or more coils, for example made of a wrapped cable or a band as shown, usually forming a generally circular annulus with a coil axis and a transverse diameter generally perpendicular to the coil axis. When a torque is applied to a spiral torsion spring, an angular displacement between the first and second loading points is created, the coil deflects, and the material from which it is made is placed under stress. Spiral torsion springs may form a helix; a flat spiral, conical, spherical or volute in shape; or be less than a full coil; and may be differentiated from compression and extensions springs by their application in resisting torsion. A flat spiral torsion spring provides the advantage in a shoulder brace 10 of long strap travel in a compact package. In one case each spring 26 is configured to extend up to ten, fifteen or more, for example twenty or more, inches of additional second strap part 24 under increasing tension with increasing extension.

A torsion spring can be linear or non-linear. In a linear torsion spring, the applied torque is directly proportional to the angular displacement via an unchanging variable called the spring rate. That is, the ratio between applied torque and angular displacement is constant. In a non-linear torsion spring, the applied torque and angular displacement are not proportional. There are two types of non-linear torsion springs, hardening and softening. In a hardening torsion spring, the ratio between applied torque and angular displacement grows such that with the application of an additional degree increase in angular displacement, more additional torque will be required than would be required for a linear spring.

In one case the spring 26 tested was a flat spiral torsion spring, whose dimensions and properties are listed below in Table 1. The deflection exceeded the turns to set, stress exceeds tensile strength, and the spring had a liner applier torque/angular displacement relationship.

TABLE 1

| spring properties | |
|---|---|
| Material | Stainless 301 |
| Spring Width [in] | 0.5 |
| Arbor Diameter [in] | 0.375 |
| Free Coils | 10 |
| Material Thickness [in] | 0.032 |
| Min. Free Diameter [in] | 2.25 |
| Thickness Tolerance [in] | +/−0.00100 |
| Turns to Set | 1.897 |
| Spring Weight [lb] | 0.188 |
| Available Turns | 5.2235 |
| Active Length [in] | 41.2334 |
| Torque [lbf-in] | 30.285 |
| Deflection [turns] | 5.199 |
| Stress [psi] | 354902 |
| % of Area Filled | 34.1 |

In one case a compression or extension spring may be used, such as a simple coil spring, or an elastic strap or band may be used, or another suitable biasing device may be used. A spiral torsion spring may include a long coil that itself is coiled in a spiral (a coil of a coil). A spring or strap retractor may be attached to both ends of each strap 20. In some cases the spring 26 thickness is 0.032" or thinner, though other ranges of thickness may be used. In some cases each strap retractor comprises dual spiral torsion springs mounted coaxially to one another, and in one case a pair of spiral torsion springs mounted coaxial to one another forms a single strap retractor for both straps 20. The top cover 52 may be removable.

Suitable hinges 70 include piano hinges, living hinges, barrel hinges, and others. Should straps may each extend from the support structure 16, over the collar bone, under a respective armpit, and back to the support structure 16. In other cases shoulder straps may cross on another or cross the chest laterally, such that one shoulder strap starts from the left housing and wraps around the user's chest and back to the right housing, and vice versa. Spring housings 18A, 18B may have puck shapes. Where two components are secured or connected, such may be accomplished via suitable securing mechanisms such as fasteners, adhesives, welding, sewing, or others.

The free end of the second strap part 24 may connect directly to the spring 26 in some cases. Parts described for the base 50 may be applicable to the top cover 52, and vice versa. Instead of or in addition to bearings 46, an annular bearing may be mounted circumferentially around spool 36, or a belt or other suitable bearing may be used. Pads and padding may be made of a material that is comfortable to be worn or pressed against the user for long periods of time, for example foam. A lock may be provided in association with each strap retractor for restricting strap travel, for example to permit the brace 10 to be switched into a clavicle brace mode where no strap movement is permitted. A lock may also limit strap travel beyond a predetermined range that is smaller than the full range of travel provided by springs 26, for example to permit movement over several inches.

The torque adjuster 90 and the buckle 110 may be combined in a single unit in some cases. Pre-torqueing may be accomplished by mechanisms other than or in addition to torque adjuster 90 on strap 20. For example, a mechanism may be provided on each housing 18 to pre-torque (twist) the anchor end 30 relative to the housing 18. An example of the latter is a lever, such as a dial, formed by or mounted to the top plate 55, connected to rotate the arbor 32 relative to the housing 18, with a ratchet mechanism, such as a series of teeth and teeth receivers, between the dial and the housing 18 for maintaining a selecting pre-torque setting, and in some cases a release mechanism is provided for the ratchet. In some cases the brace 10 may be configured to carry a non-zero tension between torque adjuster 90 and spring 26 when in a position corresponding to a maximum length, of second strap part 24 between adjuster 90 and free end 28 of spring 26, to reduce the occurrence of bunching or misalignment of strap part 24 in the housing 18. Instead of a reducer 90, the first and second strap parts may be directly connected, for example by stitching. The strap may comprise breathable material, such as synthetic leather, which absorbs moisture and is washable and soft.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A shoulder brace comprising:
   a support structure;
   a plurality of flat spiral torsion springs mounted to the support structure; and
   left and right shoulder straps each having a first strap part connected to the support structure and a second strap part connected to a free end of a respective flat spiral torsion spring.

2. The shoulder brace of claim 1 in which the support structure comprises left and right housings that are connected via a hinge and each mount a respective flat spiral torsion spring.

3. The shoulder brace of claim 2 in which each of the left and right housings have an upper-back-contacting base and a top cover that collectively define an interior compartment mounting a respective flat spiral torsion spring.

4. The shoulder brace of claim 3 in which each of the left and right housings further comprise a strap port, defined between the interior compartment and an exterior, through which the respective left or right shoulder strap passes.

5. The shoulder brace of claim 4 in which each of the left and right housings further comprise a spool that is within the interior compartment and secured to the free end of the respective flat spiral torsion spring, the spool mounting the second strap part of the respective left or right shoulder strap.

6. The shoulder brace of claim 5 in which each of the left and right housings comprise spool bearings that are located within the interior compartment.

7. The shoulder brace of claim 6 in which the spool bearings are located adjacent opposed first and second lateral walls, respectively, that define the strap port.

8. The shoulder brace of claim 7 in which, for each of the left and right housings, the spool bearings are bushing sleeves positioned on respective posts.

9. The shoulder brace of claim 4 further comprising a torque adjuster between the first strap part and the second strap part for adjusting the length of the second strap part between the torque adjuster and the free end of the respective flat spiral torsion spring.

10. The shoulder brace of claim 9 in which the shoulder brace is configured to have a pre-torqued neutral position where each torque adjuster seats against a seating surface associated with a respective strap port to apply a non-zero tension to a respective flat spiral torsion spring through the respective second strap part.

11. The shoulder brace of claim 3 in which each top cover is connected to a respective base via the hinge.

12. The shoulder brace of claim 3 in which each of the left and right housings secure an anchor end of the respective flat spiral torsion spring.

13. The shoulder brace of claim 6 in which the spool bearings comprise one or more lateral projections.

14. The shoulder brace of claim 2 in which the left and right housings comprise respective upper-back-contacting pads that cooperate in use to space the support structure and hinge out of contact with skin overlying a user's spine.

15. The shoulder brace of claim 2 in which the hinge comprises a left hinge and a right hinge, and the left and right housings are separated by a spacer part that connects to the left and right housings via the left hinge and the right hinge, respectively.

16. The shoulder brace of claim 2 in which the support structure has a clamshell design with a deployed position where the left and right housings are spread apart from one another, and a folded position where the left and right housings stack one on top of the other.

17. The shoulder brace of claim 1 in which a coil axis of each flat spiral torsion spring is perpendicular to a contact plane defined by an upper-back-contacting surface of the support structure.

18. The shoulder brace of claim 1 in which one or both of the left and right shoulder straps comprise a buckle and a length adjuster on the first strap part.

19. A method comprising:
positioning a support structure against a user's upper back, the support structure having a plurality of spiral torsion springs;
looping left and right shoulder straps around a user's left and right shoulders, respectively; and
in which each of the left and right shoulder straps connects to the support structure via a respective spiral torsion spring for applying tension through the respective left or right shoulder strap to pull the user's shoulders back.

20. A shoulder brace comprising:
a housing;
strap retractors mounted within the housing;
left and right shoulder straps each having a first strap part, a second strap part, and a torque adjuster, in each first strap is connected to the housing, each second strap part passes through a respective strap port in the housing to connect to a respective strap retractor, and each torque adjuster is between the first strap part and the second strap part for adjusting the length of the second strap part between the torque adjuster and the respective strap retractor; and
in which the shoulder brace is configured to have a pre-torqued neutral position where each torque adjuster seats against the respective strap port and applies a non-zero tension to the respective strap retractor through the respective second strap part.

* * * * *